United States Patent [19]
Lindley et al.

[11] Patent Number: 5,935,998
[45] Date of Patent: Aug. 10, 1999

[54] USE OF ALL ALLYLAMINE DERIVATIVES SUCH AS TERBINAFINE, IN THE MANUFACTURE OF A MEDICAMENT FOR THE TREATMENT OF *HELICOBACTER PYLORI* INFECTION OR ASSOCIATED DISEASES

[75] Inventors: Ivan James Dalton Lindley, Brunn/Gebirge; Neil Stewart Ryder, Vienna, both of Austria

[73] Assignee: Novartis AG, Basel, Switzerland

[21] Appl. No.: 08/981,324

[22] PCT Filed: Jul. 5, 1996

[86] PCT No.: PCT/EP96/02970

§ 371 Date: Jan. 6, 1998

§ 102(e) Date: Jan. 6, 1998

[87] PCT Pub. No.: WO97/02026

PCT Pub. Date: Jan. 23, 1997

[30] Foreign Application Priority Data

Jul. 6, 1995 [GB] United Kingdom .................. 9513750

[51] Int. Cl.⁶ ................ A61K 31/27; A61K 31/495; A61K 31/135
[52] U.S. Cl. ................ 514/481; 514/249; 514/650; 514/655; 514/925; 514/926; 514/927
[58] Field of Search ................ 514/249, 650, 514/655, 481, 925, 926, 927

[56] References Cited

U.S. PATENT DOCUMENTS

| | | | |
|---|---|---|---|
| 4,282,251 | 8/1981 | Berney | 424/316 |
| 4,755,534 | 7/1988 | Stuetz et al. | 514/655 |
| 4,894,375 | 1/1990 | Gadebusch et al. | 514/249 |
| 5,132,459 | 7/1992 | Stuetz et al. | 564/387 |
| 5,348,746 | 9/1994 | Dong et al. | 424/473 |

FOREIGN PATENT DOCUMENTS

| | | |
|---|---|---|
| 0 000 896 | 3/1979 | European Pat. Off. . |
| 0024587 | 3/1981 | European Pat. Off. . |
| 0410359 | 1/1991 | European Pat. Off. . |
| 43 17 449 A1 | 11/1994 | Germany . |
| 2 051 799 | 1/1981 | United Kingdom . |

OTHER PUBLICATIONS

Derwent Abstract 95:000525/01 corresponding to DE 43 17 449.

King D. et al., "In Vitro Activities of Econazole Nitrate and Terbinafine Against Fungal and Bacterial Pathogens Commonly Encountered in Podiatric Practice", Advances in Therapy, vol. 11, No. 3, 1994, pp. 120–131.

Nolting S., "Clinical Relevance of the Antibacterial Activity of Terbinafine: A Contralateral Comparison Between 1% Terbinafine Cream and 0.1% Gentamicin Sulphate Cream in Pyoderma", British Journal of Dermatology, vol. 126, 1992, pp. 56–60.

Weil M. et al., "Topical Econazole Versus Terbinafine in the Treatment of Toe Web Space Infections: A Comparison", Advances in Therapy, vol. 13, 1996, pp. 355–364.

"Activity of the antimycotic ketoconazole against Helicobacter pylori", J. Antimicrob, Chemother., vol. 30, 1992, pp. 238–240.

Am. J. Gastroenterol., vol. 89, 1994, pp. 1603–1604.

Eur. J. Clin. Microbiol. Infect. Dis., vol. 11, 1992, pp. 273–274.

J. Micologie Medicale (France), vol. 5, 1995, Suppl. 1., pp. 17–20.

Stütz et al., "Synthesis and Structure–Activity Correlations within Allylamine Antimycotics", Ann. N.Y. Acad. Sci., vol. 544, 1988, pp. 46–62.

von Recklinghausen et al., "Activity of Antibiotics and Azole Antimycotics Against Helicobacter pylori", Int. J. Med., Micr., vol. 280, 1993, pp. 279–285.

Y. Glupczynski, "In vitro Susceptibility Testing of Helicobacter pylori to Antimicrobial Agents: Basis for Treatment or Microbiologists' Obession?", Int. J. Med. Micr., vol. 280, 1993, pp. 227–238.

Jensen, J.C., "Pharmacokinetics of Lamisil in Humans," J. Derm. Treatment, vol. 1, No. Suppl. 2, (1990), pp. 15–8.

*Primary Examiner*—Kevin E. Weddington
*Attorney, Agent, or Firm*—Carol A. Loeschorn

[57] ABSTRACT

Use of compounds of formula (I), wherein R has various significances, in free base form or in pharmaceutically acceptable salt form, as agents against H. pylori infection and associated diseases.

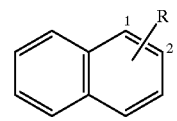

(I)

9 Claims, No Drawings

USE OF ALL ALLYLAMINE DERIVATIVES SUCH AS TERBINAFINE, IN THE MANUFACTURE OF A MEDICAMENT FOR THE TREATMENT OF *HELICOBACTER PYLORI* INFECTION OR ASSOCIATED DISEASES

This is a 371 of PCT/EP96/02970, filed Jul. 5, 1996.

The invention relates to a new therapeutic use of certain allylamine compounds.

Allylamines are known for being squalene epoxidase inhibitors and exhibit antimycotic activity. Surprisingly it was now found that some compounds of this class are also active against *Helicobacter pylori* (*Campylobacter pylordis*).

Members of the genus Helicobacter are gram-negative spiral bacteria that are usually found in the mucus layer of the stomach of humans and animals. They are microaerophilic, possess flagella, and produce numerous extracellular products, including urease, proteases, and other compounds that enable them to survive in the hostile environment of the stomach. Worldwide, approximately half of the human population are H.pylori-positive. Without eradication therapy, established *Helicobacter pylori* infection seems to persist for life. H.pylori infection regularly results in chronic active gastris (type-B gastritis), but rarely becomes clinically evident. Recently, a causal relationship between H.pylori infection and peptic ulcer disease has been proven.

Furthermore, on the basis of previous epidemiological evidence, H.pylori has been classified as a category 1 (definite) human carcinogen by the WHO (World Health Organization). The difficulties faced in assessing the risk of gastric cancer in different susceptible populations have been addressed and new data presented to support a model of chronic gastritis leading to atrophy, followed by intestinal metaplasia and gastric cancer.

It has now been found that some compounds of the allylamine class of antimycotics exhibit excellent inhibitory activity against IH.pylori. They are therefore useful in the therapy in the above mentioned diseases.

The, invention concerns the use of a compound of formula I

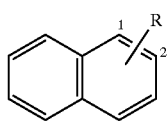

wherein
either R is attached at the 1 or 2 position of the naphthyl ring and is

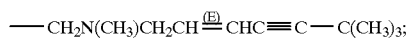

or R is attached at the I position and is

or N-[(E)-3-phenyl-2-propenyl]-2-piperlidnyl, in free base form or in pharmaceutically acceptable salt form, in the therapy of *Helicobacter pylori* infection and associated diseases such as gastritis, peptic ulcer, duodenal ulcer, gastric atrophy, intestinal metaplasia, non-ulcerative dyspepsia, MALT lymphoma (lymphoma of gastric mucosa—associated lymphatic tissue), non-Hodgkin's lymphoma and gastric cancer, hereinafter briefly named "the use of the invention".

It also concerns the use of a compound of formula I as defined above in fee base form or in pharmaceutically acceptable salt form for the manufacture of a medicament for use in the therapy of *Helicobacter pylori* infection and associated diseases as defined above, optionally in combination with one or more other, preferably orally active agents.

It further concerns a method of treatment of *Helicobacter pylori* infection and associated diseases as defined above, comprising administration of a therapeutically effective amount of a compound of formula I as defined above in free base form or in pharmaceutically acceptable salt form to a subject in need of such treatment. Administration may optionally be effected in combination with one or more other, preferably orally active agent.

It further concerns an agent for use in the therapy of *Helicobacter pylori* infection and associated diseases as defined above, comprising a compound of formula I in free base form or in pharmaceutically acceptable salt form together with at least one pharmaceutically acceptable carrier or diluent, optionally in combination with one or more other, preferably orally active agents.

The invention further concerns a process for the preparation of a medicament for use as defined above, which comprises mixing a compound of formula I in free base form or in pharmaceutically acceptable salt form optionally in combination with one or more other, preferably orally active agents together with at least one pharmaceutically acceptable carrier or diluent.

It also concerns a pharmaceutical composition adapted for use as defined above, which comprises a compound of formula I in free base form or in pharmaceutically acceptable salt form optionally in combination with one or more other active agents and is compounded as an orally administrable capsule shell or drink solution for release and activity in the gastrointestinal system.

The compounds of formula I in free base or salt form, methods for their preparation and their use as antimycotics, are known from e.g. EP 24587, U.S. Pat. No. 4,282,251, EP 00896, GB 2,051,799 and/or A. Stütz, *Ann. N.Y. Acad. Sci.* 544 (2988) 46–62.

A compound of formula I may exist in free base form or in salt, particularly acid addition salt form. It preferably is in salt form, e.g. the hydrochloride salt form. When R includes the 2-piperidinyl moiety it may also be in optically active form, e.g. as the (R)(+)enantiomer.

R preferably is attached at the 1 position. R preferably includes a triple bond. R especially is attached at the 1 position and includes a triple bond; when that compound is in hydrochloride salt form it is known as terbinafine (Lamisil®) A subgroup of compounds of formula I is the compounds of formula I as defined above, with the exception of terbinafine.

The term "therapy" should be understood to apply for prophylactic as well as curative treatment. The subject suffering from H.pylori infection preferably is not suffering from, or is not being treated for, mycotic infection; in a subgroup the subject suffering from H.pylori infection preferably is not suffering from, or is not being treated for, mycotic, ringworm or yeast infection.

The activity of the compounds of formula I against Helicobacter pylori can be verified e.g. by determination of the MIC (minimum inhibitory concentration) in the following test method using various clinical isolates of H.pylori:

Clinical isolates of H.pylori are stored at −70° C. in Brucella broth with 20% glycerol. All isolates are subcultured on fresh blood agar Blood agar base No. 2, Unipath, with 5% defibrinated horse blood) and confirmed as *Helicobacter pylori* by Gram shin, catalase, oxidase and rapid-urease tests. Initial incubation is carried out microaerobically in a variable-atmosphere incubator (6% $O_2$, 10% $CO_2$, 3% $H_2$, 81% $N_2$) at 37° C. Subcultures and MIC tests are carried out in humidified air with 5% $CO_2$ at 37° C. Test compounds are incorporated into Mueller-Hinton agar (Unipath) with 7% defibrinated horse blood at pH 7.2. After growth for 72 hours on blood agar H.pylori suspensions are made in Brucella broth (Unipath) equivalent to McFarland standard No. 3. This represents $10^8$ cfu/ml H.pylori. A multipoint inoculator will deliver 1 $\mu$l per spot (approximately $10^5$ cfu). The type strain NCTC 11637 is used as a control in each run. Plates are incubated for 72 hours and the MIC is taken as the lowest concentration of test compound to completely inhibit growth. All tests are carried out in triplicate.

In the above test the compounds of formula I have a MIC of from about 0.06 mg/l to about 30 mg/l. Thus, the compound of formula R in R(+)-enantiomeric and hydrochloride salt form and wherein R is N-[(E)-3-phenyl-2-propenyl-2-piperidinyl attached at the 1 position is found to have MIC values of 0.06–4 mg/l, the remaining three compounds of formula H in hydrochloride salt form, MIC values of 8–32 mg/l.

The compounds of formula I in free base form or in pharmaceutically acceptable salt form are therefore useful as agents in the therapy of Helicobacter pylori infection and associated diseases such as gastritis, peptic ulcer, duodenal ulcer, atrophy, intestinal metaplasia, non-ulcerative dyspepsia, MALT lymphoma, non-Hodgkin's lymphoma and gastric cancer. For this use, the effective dosage will, of course, vary depending on the particular agent employed, the mode of administration and the treatment desired. However, in general, satisfactory results are obtained when the agents are administered at a daily dosage of from about 0.02 mg/kg to about 50 mg/kg animal body weight, suitably given in divided doses two to four times daily. For most large mammals the total daily dosage is from about 1 mg to about 3500 mg, preferably from about 10 mg to about 2000 mg, especially from about 500 mg to about 1500 mg, especially from about 550 mg to about 1200 mg, especially about 600 mg, given once or twice daily. They may be administered in similar manner to known standards for use in such indications. It is indicated that for this use they may be administered to larger mammals, for example humans, by similar modes of administration at similar or lower dosages than conventionally employed with known standards for such indications.

The usefulness of the compounds of formula I in flee base or in pharmaceutically acceptable salt form in the above indications is also indicated in standard clinical trials. A representative clinical trial may be effected as follows:

The trial is conducted employing a group of volunteers (mixed male and female of average body weight) identified as exhibiting H.pylori infection as assessed by e.g. an appropriate breath test (urease test) or antibody test, and are then given an endoscopic examination. Subjects selected are primarily selected from long-term sufferers and non-responders to conventional therapy. Each subject receives a composition in accordance with the invention, e.g. a tablet. Compositions are applied orally in an amount of from about 10 mg to about 1000 mg. Administration is effected 1, 2 or 3 times daily. Treatment is continued for each subject for a period between 7 days and 10 weeks, preferably about 2 to 4 weeks. After a further period without treatment of between 7 days and 6 weeks, preferably about 4 weeks, a second assessment by e.g. breath test is given to determine the H.pylori status of the subject, and a second endoscopic examination is effected. Alternative treatment is withdrawn prior to and during treatment with the compound to be tested. Each subject undergoes full gastric examination prior to commencement of treatment to determine extent, location and severity of lesions. Each subject is also questioned to determine subjective experience of the disease. Examination is repeated at the conclusion of treatment and all changes in condition are noted. At the conclusion of treatment each subject is again questioned to determine subjective experience of the disease. All changes in the subjects' condition, especially extent, intensity of lesion as well as any side effects, are noted, with particular emphasis on the determination of eradication off H.pylori. Results obtained on administration of composition in accordance with the invention are compared with those obtained for a control group receiving a placebo composition not comprising the compound to be tested. Results obtained show marked reduction of gastritis in subjects receiving compositions in accordance with the invention administered as described as compared with control groups receiving placebo. Compositions in accordance with the invention tested are found to be well tolerated.

The agents are well tolerated. The acute toxicity in the mouse of representative compounds of formula I is as follows:

compound of formula I in hydrochloride salt form and wherein R is attached at the 1 position and is

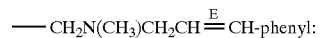

$LD_{50}$ p.o. >1000 mg/kg; $LD_{50}$ i.p.: ≈560 mg/kg;

compound of formula I in hydrochloride salt form and wherein R is attached at the 1 position and is

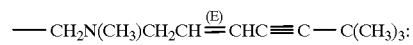

LD50 p.o. >1000 mg/kg; LD50 i.p. =790 mg/kg.

The tolerability of other compounds failing under the scope may be determined in conventional manner, and is indicated to be of the same order as that of the representative examples above.

The agents are optionally administered in combination with one or more other, preferably orally active agents such as an $H_2$ receptor blocker, e.g. cimetidine, ranitidine or famotidine, an azole such as omeprazol or metronidazol, or a basic aluninium complex such as sucralfate. The dosages of the components of such combinations are similar or lower than conventionally employed.

The compounds of formula I in free base form or in pharmaceutically acceptable salt form, optionally in combination with one or more other, preferably orally active agents may be admixed with conventional chemotherapeutically acceptable diluents and carriers and administered e.g. parenterally or intravenously, preferably orally, in such forms as tablets or capsules. The concentrations of active substance will, of course, vary depending e.g. on the compound employed, the treatment desired and the nature of the form.

The pharmaceutical compositions for oral use are preferably compounded in unit dosage form, for example by filling them into orally administrable capsule shells. The capsule shells may be soft or hard gelatine capsule shells. However, if desired the pharmaceutical compositions may be in a drink solution form and may include water or any other aqueous system, to provide emulsion or microemulsion systems suitable for drinking.

We claim:

1. A method of treatment of *Helicobacter pylori* infection and associated diseases comprising administration of a therapeutically effective amount of a compound of formula I

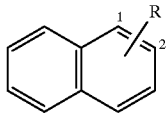

wherein
either R is attached at the 1 or 2 position of the naphthyl ring and is

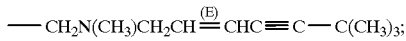

or R is attached at the 1 position and is

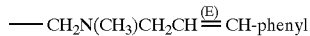

or N-[(E)-3-phenyl-2-propenyl]-2-piperidinyl in free base form or in pharmaceutically acceptable salt form, to a subject in need of such treatment.

2. A method according to claim 1 wherein the compound of formula II has R attached at the 1 position of the naphthyl ring and R is

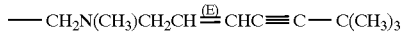

in free base form or pharmaceutically acceptable salt form.

3. A method according to claim 2 wherein the compound of formula is in a pharmaceutically acceptable salt form.

4. A method according to claim 3 wherein the compound of formula is in the form of a hydrochloride salt.

5. A method according to claim 1 wherein *Helicobacter pylori* infection and associated diseases are selected from the group consisting of gastritis, peptic ulcer, duodenal ulcer, gastric atrophy, intestinal metaplasia, non-ulcerative dyspepsia, MALT lymphoma, non-Hodgkin's lymphoma and gastric cancer.

6. A method according to claim 1 wherein said compound of formula I is administered to the subject in combination with one or more other orally active agents.

7. A method according to claim 6 wherein said other orally active agents are selected from the group consisting of cimetidine, ranitidine, famotidine, omeprazol, inetronidazol and sucralfate.

8. A method according to claim 1 wherein said compound of formula is compounded as an orally administrable capsule shell or drink solution.

9. A method according to claim 6 wherein said other orally active agent is cimetidine.

* * * * *

UNITED STATES PATENT AND TRADEMARK OFFICE
CERTIFICATE OF CORRECTION

PATENT NO. : 5,935,998
DATED : August 10, 1999
INVENTOR(S) : LINDLEY ET AL.

It is certified that error appears in the above-identified patent and that said Letters Patent is hereby corrected as shown below:

Title page, left column, section [54] and column 1, lines 1-6 should read:

-- [54] USE OF ALLYLAMINE DERIVATIVES SUCH AS TERBINAFINE, IN THE MANUFACTURE OF A MEDICAMENT FOR THE TREATMENT OF *HELICOBACTER PYLORI* INFECTION OR ASSOCIATED DISEASES-- .

column 6, claims 3, 4 and 8, second line, add I after the word formula--

Signed and Sealed this

Nineteenth Day of September, 2000

Attest:

Q. TODD DICKINSON

*Attesting Officer*   *Director of Patents and Trademarks*

UNITED STATES PATENT AND TRADEMARK OFFICE
CERTIFICATE OF CORRECTION

PATENT NO. : 5,935,998
DATED : August 10, 1999
INVENTOR(S) : LINDLEY ET AL.

It is certified that error appears in the above-identified patent and that said Letters Patent is hereby corrected as shown below:

Under column 6, claim 2, second line, change formula II to formula I.

Signed and Sealed this

Twenty-first Day of November, 2000

Attest:

Q. TODD DICKINSON

Attesting Officer

Director of Patents and Trademarks